(12) United States Patent
Seykora et al.

(10) Patent No.: US 10,201,358 B2
(45) Date of Patent: Feb. 12, 2019

(54) ARTICULATING SYNDESMOSIS TARGETING GUIDE DEVICE AND METHOD

(71) Applicant: Acumed LLC, Hillsboro, OR (US)

(72) Inventors: Andrew W. Seykora, Portland, OR (US); James W. Michelinie, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 614 days.

(21) Appl. No.: 14/752,631

(22) Filed: Jun. 26, 2015

(65) Prior Publication Data

US 2016/0310191 A1    Oct. 27, 2016

Related U.S. Application Data

(60) Provisional application No. 62/150,738, filed on Apr. 21, 2015.

(51) Int. Cl.
| | | |
|---|---|---|
| *A61B 17/17* | (2006.01) | |
| *A61B 17/88* | (2006.01) | |
| *A61B 17/56* | (2006.01) | |
| *A61B 17/80* | (2006.01) | |
| *A61B 17/90* | (2006.01) | |
| *A61B 17/70* | (2006.01) | |

(52) U.S. Cl.
CPC ...... *A61B 17/1775* (2016.11); *A61B 17/1739* (2013.01); *A61B 17/1764* (2013.01); *A61B 17/88* (2013.01); *A61B 17/7037* (2013.01); *A61B 17/8061* (2013.01); *A61B 2017/564* (2013.01); *A61B 2017/90* (2013.01)

(58) Field of Classification Search
CPC ............ A61B 17/1725; A61B 17/1728; A61B 17/1775; A61B 17/8872; A61B 17/8897; A61B 17/1764; A61B 17/88
See application file for complete search history.

(56) References Cited

U.S. PATENT DOCUMENTS

| | | |
|---|---|---|
| 2,961,900 A | 11/1960 | Stanton et al. |
| 3,664,022 A | 5/1972 | Small |
| 4,465,065 A | 8/1984 | Goffried |
| 4,708,139 A | 11/1987 | Dunbar, IV |
| 4,733,654 A | 3/1988 | Marino |
| 4,865,025 A | 9/1989 | Buzzi et al. |
| 4,917,604 A | 4/1990 | Small |

(Continued)

FOREIGN PATENT DOCUMENTS

WO            0025681 A1    5/2000

*Primary Examiner* — Howie Matthews
(74) *Attorney, Agent, or Firm* — Kolisch Hartwell, P.C.

(57) ABSTRACT

Aligning the syndesmosis joint by a novel device and method includes establishing a first plane by attaching a bone plate to the posterolateral aspect of the distal fibula. A second transverse plane arranges perpendicular to the first nominal plane. A syndesmosis targeting guide device includes a post having a post axis extending perpendicular to the first plane and in the second plane. The device includes a curvilinear slider guide extending along an arc in the second plane. The slider is positioned to a first position and fixing that first position to establish a fixed entry point in the fibula wherein the fixed entry point lies in the second plane and further thereby establishing a desired trajectory in the second plane wherein the trajectory includes the fixed entry point based on the slider first position.

20 Claims, 15 Drawing Sheets

(56) References Cited

U.S. PATENT DOCUMENTS

Figure 1:
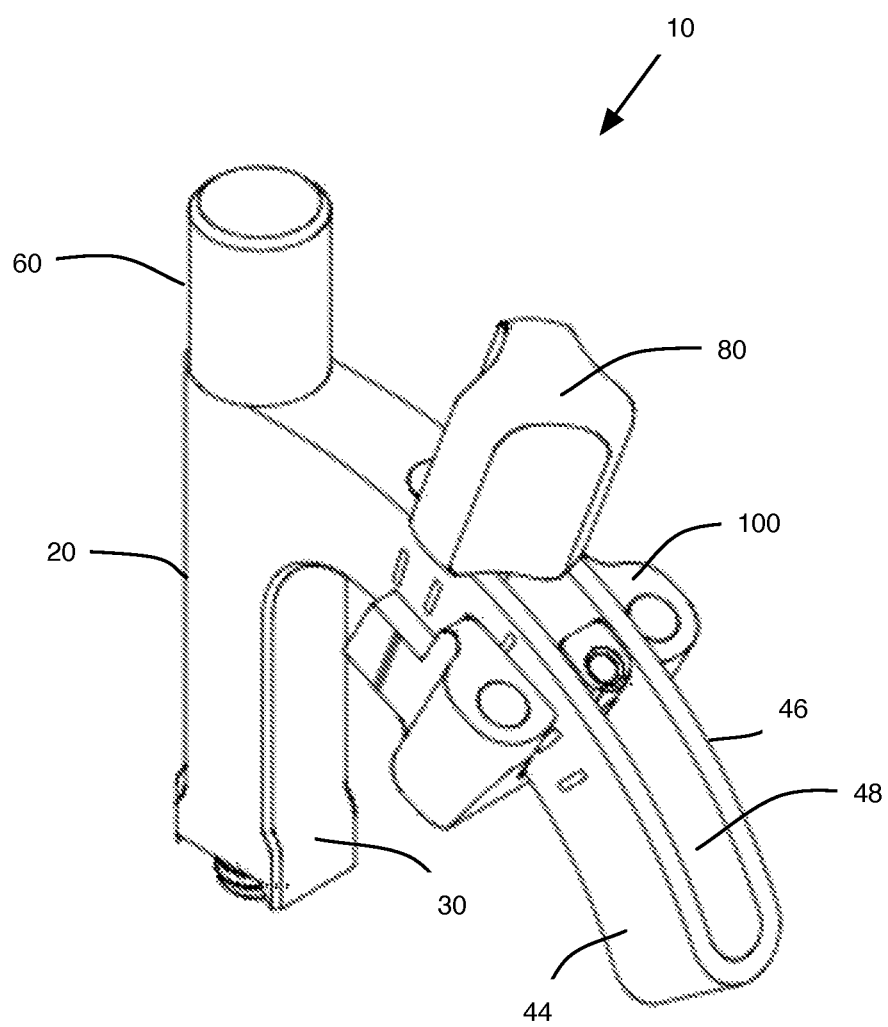

| | | |
|---|---|---|
| 5,163,940 A | 11/1992 | Bourque |
| 5,217,441 A | 6/1993 | Shichman |
| 5,356,410 A | 10/1994 | Pennig |
| 5,364,399 A | 11/1994 | Lowery et al. |
| 5,423,826 A | 6/1995 | Coates et al. |
| 5,429,641 A | 7/1995 | Goffried |
| 5,458,602 A | 10/1995 | Goble et al. |
| 5,458,654 A | 10/1995 | Tepic |
| 5,562,664 A | 10/1996 | Durlacher et al. |
| 5,613,971 A | 3/1997 | Lower et al. |
| 5,676,666 A | 10/1997 | Oxland et al. |
| 5,688,284 A | 11/1997 | Chervitz et al. |
| 5,697,933 A | 12/1997 | Gundlapalli et al. |
| 5,709,686 A | 1/1998 | Talos et al. |
| 5,766,174 A | 6/1998 | Perry |
| 6,019,767 A | 2/2000 | Howell |
| 6,120,511 A | 9/2000 | Chan |
| 6,129,730 A | 10/2000 | Bono et al. |
| 6,206,886 B1 | 3/2001 | Bennett |
| 6,342,056 B1 | 1/2002 | Mac-Thiong et al. |
| 6,540,753 B2 | 4/2003 | Cohen |
| 6,692,503 B2 | 2/2004 | Foley et al. |
| 6,793,658 B2 | 9/2004 | LeHuec et al. |
| 7,011,665 B2 | 3/2006 | Null et al. |
| 7,153,309 B2 * | 12/2006 | Huebner ............ A61B 17/1728 606/96 |
| 8,313,492 B2 | 11/2012 | Wong et al. |
| 8,500,745 B2 | 8/2013 | Kuenzi et al. |
| 2002/0133172 A1 | 9/2002 | Lambrecht et al. |
| 2003/0040748 A1 | 2/2003 | Atkins et al. |
| 2003/0083661 A1 | 5/2003 | Orbay et al. |
| 2004/0006349 A1 | 1/2004 | Goble et al. |
| 2004/0102788 A1 | 5/2004 | Huebner et al. |
| 2012/0172936 A1* | 7/2012 | Horrell ............ A61B 17/0401 606/319 |
| 2014/0107798 A1 | 4/2014 | Jeng et al. |
| 2014/0114322 A1 | 4/2014 | Perez |

* cited by examiner

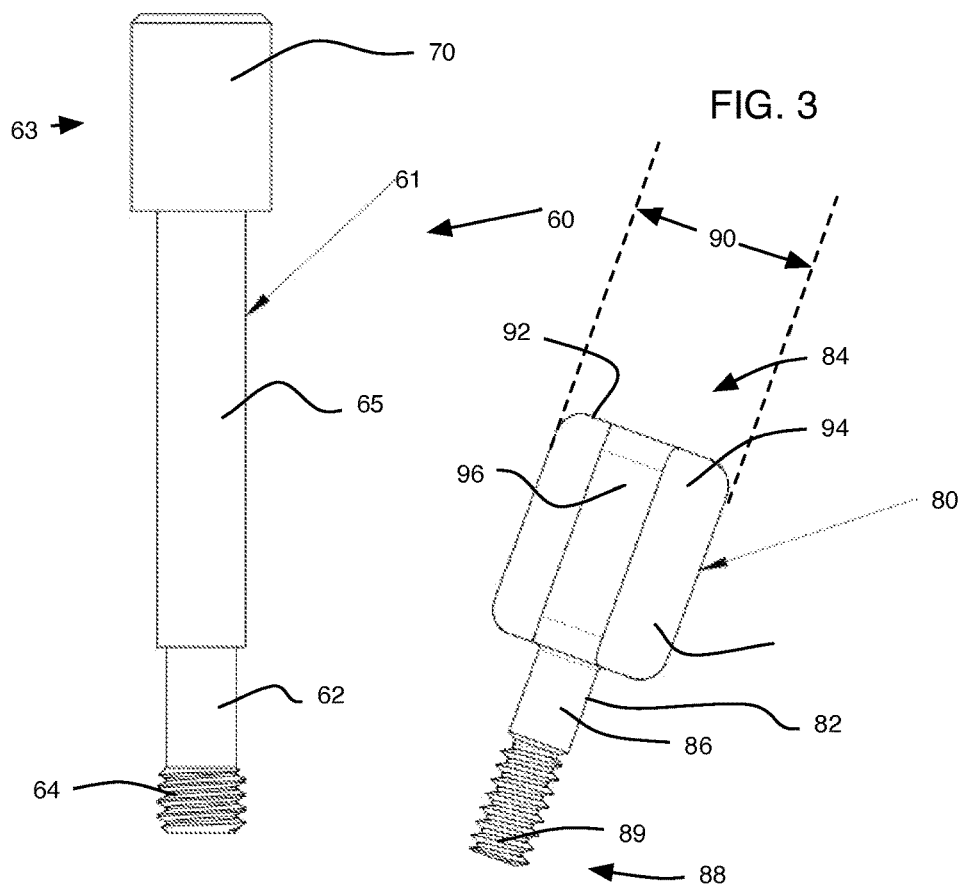
FIG. 3
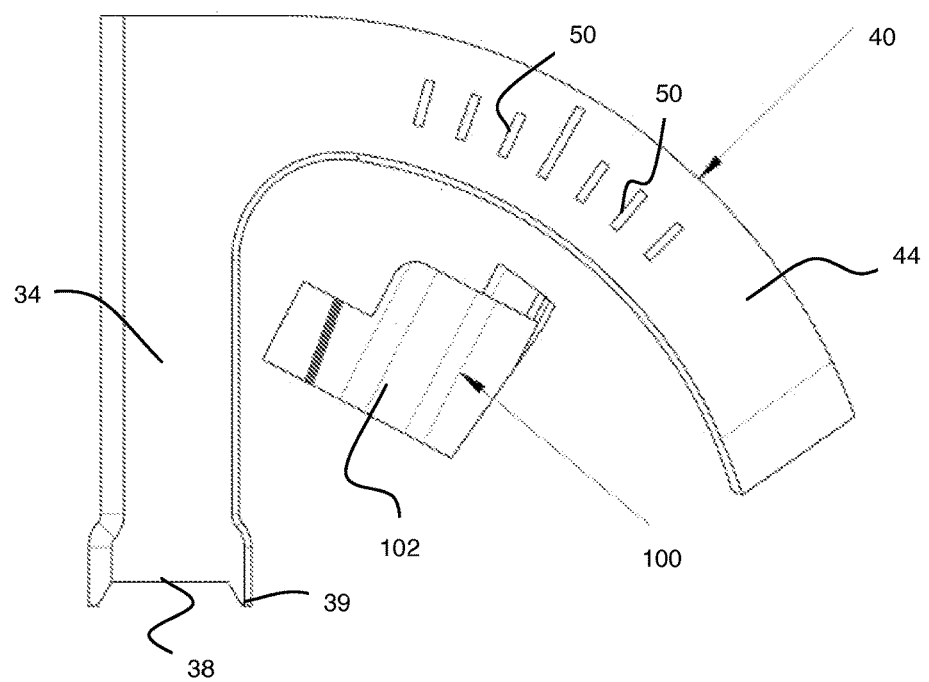

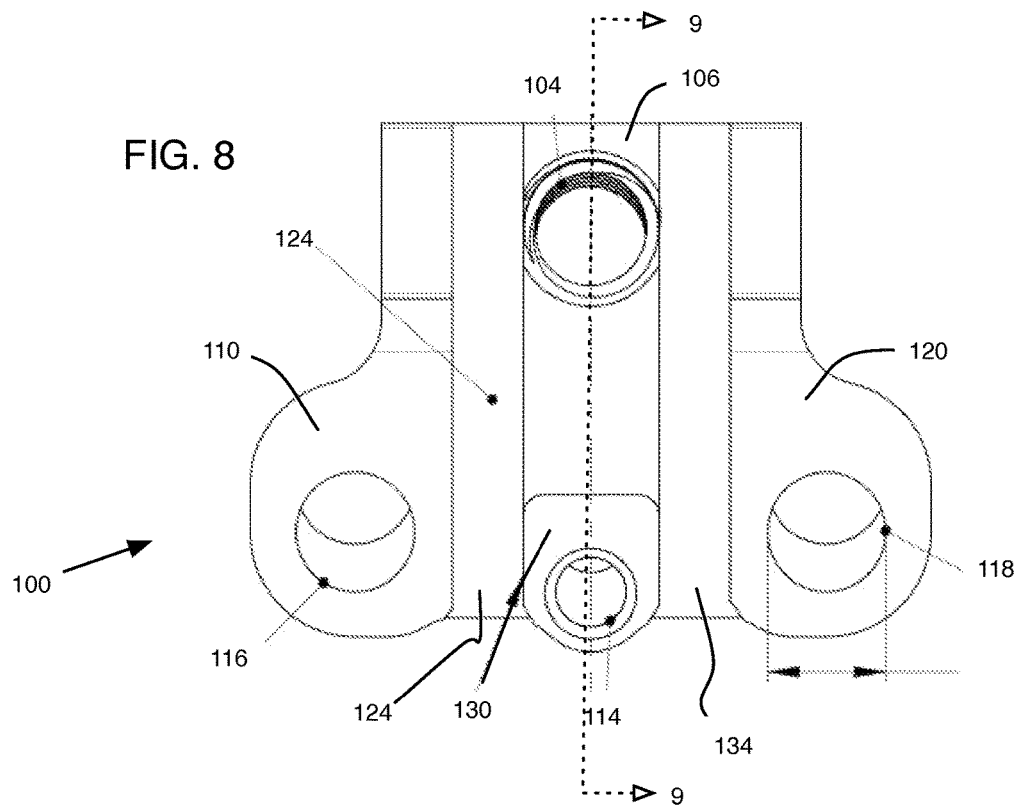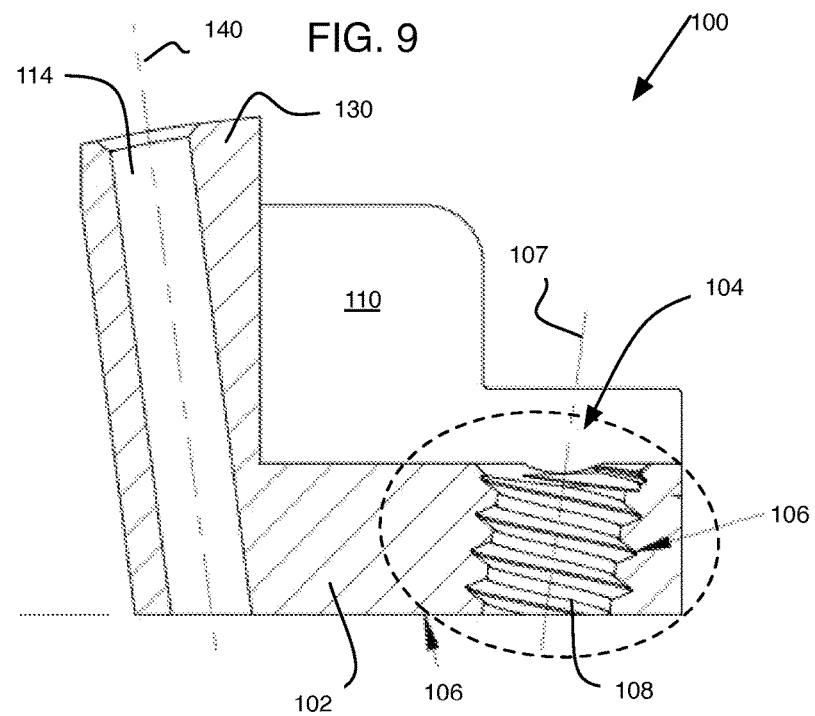

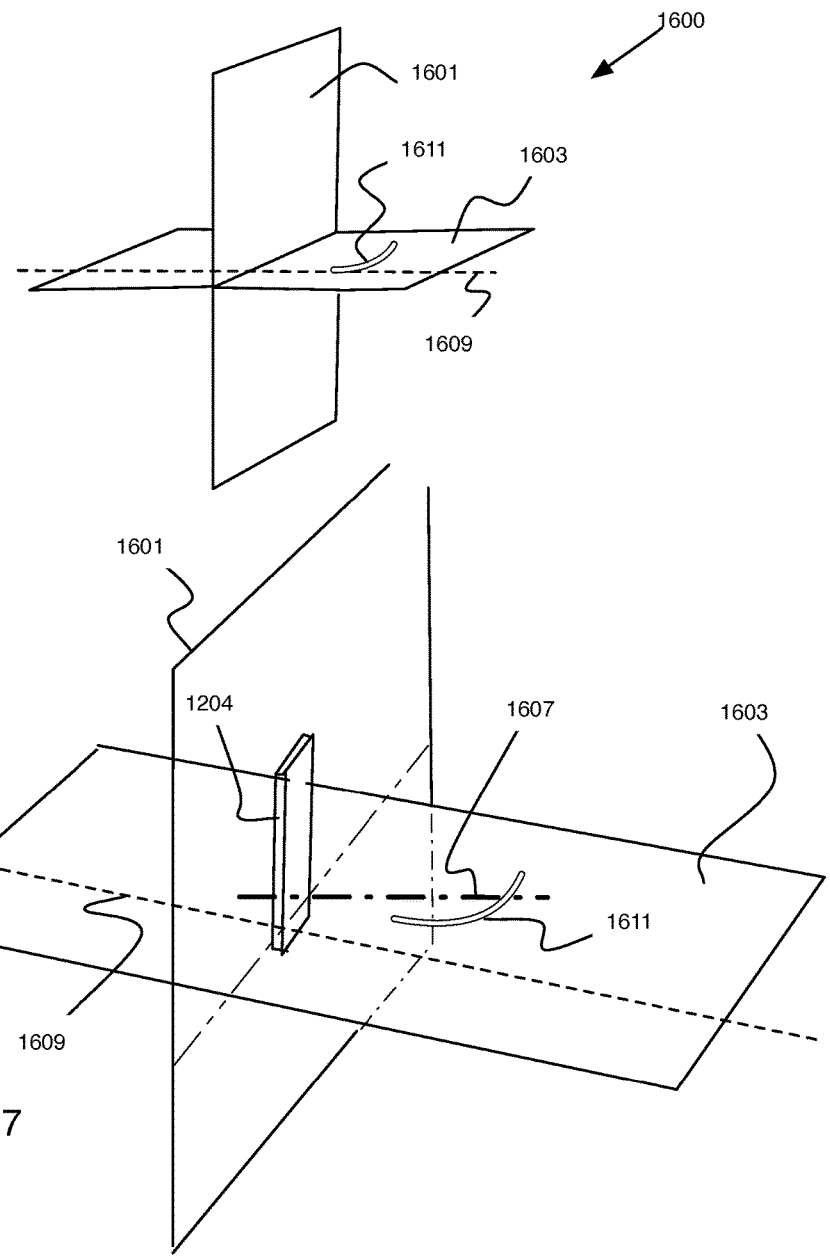

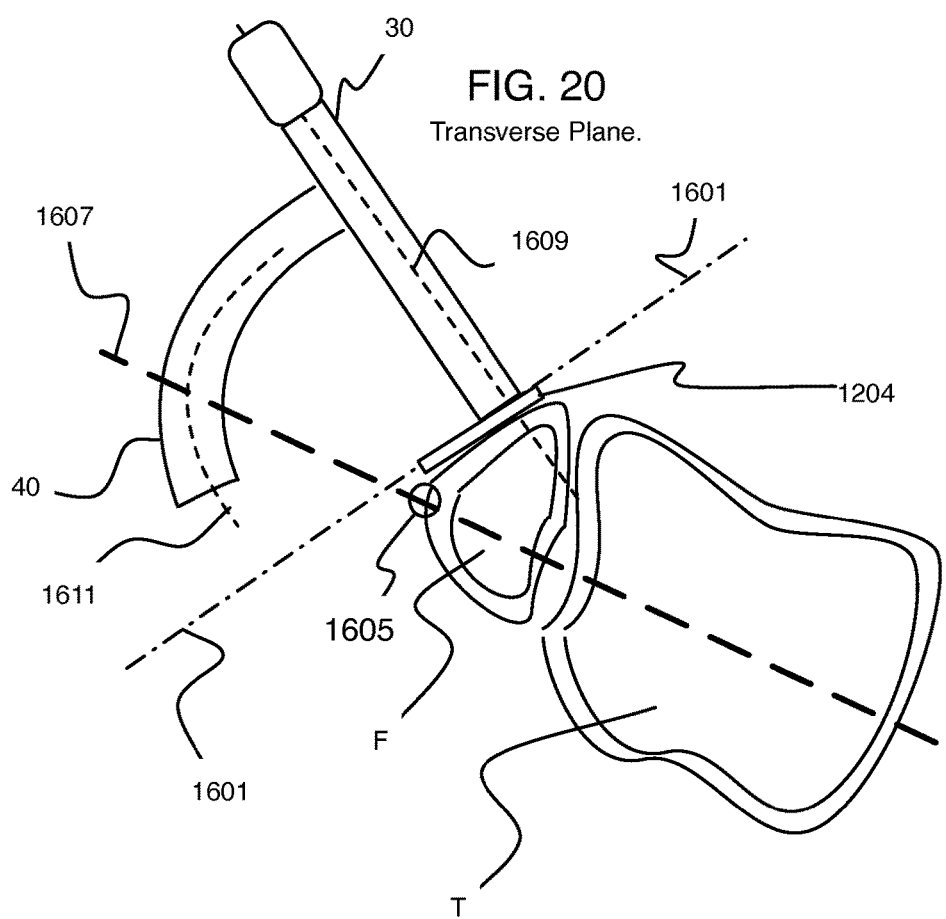

ARTICULATING SYNDESMOSIS TARGETING GUIDE DEVICE AND METHOD

PRIORITY CLAIM

The present application claims benefit under 35 USC Section 119(e) of U.S. Provisional Patent Application Ser. No. 62/150,738 filed on Apr. 21, 2015: The present application is based on and claims priority from this application, the disclosure of which is hereby expressly incorporated herein by reference.

FIELD OF THE INVENTION

The present invention relates to a device and method for repairing or immobilizing the syndesmosis. Specifically, the present invention relates to an articulating targeting and guide device, and method of use, that improves placement of implants to more accurately and more efficiently repair the syndesmosis.

BACKGROUND

The syndesmosis is a joint just above the ankle where the tibia and the fibula meet. By definition the syndesmosis is a joint and has characteristics of other joints in the body; however, it does not function like most joints, as there is very little motion between the two bones. Its main functions are, therefore, to provide stability to the ankle joint and allow motion of the joint.

Injuries to the syndesmosis are common and typically relate to an injury involving a twisting or rotation to the ankle, a broken ankle, or even a sprained ankle, resulting in stretched or torn ligaments supporting the syndesmosis.

Certain severe injuries to the syndesmosis require surgical correction to properly align and stabilize the joint so the ligaments can heal in the correct position.

Typically, surgery involves an incision over the outside of the ankle. The fibula (bone) and syndesmosis are identified and exposed. Using direct vision and live X-ray techniques, the syndesmosis, based on learned skill and judgment of the surgeon, is placed into the correct position. The surgeon then "fixes" the syndesmosis in place with an implant. This typically involves one or two screws that go from the fibula bone into the tibia bone. The screws may be placed through a plate that sits on the fibula bone. Alternatively, a suture device may be used instead of screws. A stress X-ray is performed to confirm that the syndesmosis is stable. Stitches are placed to close the incision and the leg is then placed in a splint, cast or boot.

However, syndesmosis surgery is problematic. The medical literature commonly records difficulties with properly reducing and fixating a disruption of the syndesmosis. Improper reduction and fixation of the syndesmosis arises with inaccurate placement of the syndesmosis implant. In cases where an implant is placed too anterior or posterior of the fibula or tibia the fixation device can translate the fibula resulting in malreduction of the tibio-fibular joint.

Further, current techniques in syndesmosis surgery have additional limitations. Surgeons typically drill using solid drills because cannulated screws are ill suited to syndesmosis repair. This restricts the number of attempts a surgeon can make—in contrast with other joint repairs; a surgeon can use a K-wire to visually determine the proper trajectory, remove it and make corrections if needed, and then insert a cannulated screw over the guide wire once it is in the correct position. Therefore, surgeons often have only one attempt to drill and fix the joint. Also, the distance required to drill to depth is relatively large, the typical syndesmosis screw is around 40 mm, thus a small misalignment can result is a clinically significant mal alignment. And, there is no way to use typically available operating room fluoroscopy to ensure that the drill is targeted at the center of the medial tibia. Lastly, even after insertion of the implant, visual inspection of proper fixation is only available using a computed tomography (CT) scan.

Therefore, there remains a need for a method and a device that improves the placement of implants to more accurately and more efficiently repair the syndesmosis.

SUMMARY

A guide device configured to selectively couple to a bone plate to precisely align the syndesmosis joint includes a guide body and a cooperating slider body. The guide body includes a post extending vertically, the post having a vertical centerline, at least one sidewall, and oppositely disposed top end and a bottom end; a curvilinear slider guide arranges adjacent to and extending from the top end, the curvilinear slider guide further arches downward from the top end of the post extending along an arc for greater than 20 degrees from the post, the curvilinear slider guide comprising two substantially and generally parallel sidewalls defining a slot, and the bottom end further comprising a scalloped feature configured to mate to a corresponding feature provided by the bone plate; a plate bolt configured to insert through the post of the guide body, the plate bolt comprising a distal end comprising a threaded end, the threaded end selectively engaging the plate; a guide bolt configured to insert through the slot of the guide body; and a slider configured to slideably engage the curvilinear slider guide slot and further configured to be adjustably fixed in a first position by the guide bolt.

The slider body includes a threaded hole to receive the guide bolt and associated structure to support the threaded hole including a slider-bolt post; a first guide post and a second guide post and a center wire-guide post; the first guide post disposed on a left side of the slider body, the center wire-guide post disposed at a center of the slider body and the second guide post disposed on a right side of the slider body wherein the first guide post and the center wire-guide post cooperate to define a first slot-wall-guiding channel and wherein the center wire-guide post and the second guide post cooperate to define a second slot-wall-guiding channel; the first and second slot-wall-guiding channels further comprising, respectively, an associated bottom wall and further the first and second slot-wall-guiding channels, respectively, configure to slideably engage the curvilinear slider guide slot and further whereby the guide bolt is operable to selectively fixably locate the slider in at least one position, the at least one position comprising a first position relative to the guide body; and wherein the wire-guide post defines a wire-through hole; and wherein the slider bolt post disposes on a common plane with the center wire-guide post, the slider-bolt post further configures to arrange to slide under the slot of the guide body.

Contemplated and preferred embodiments of the present invention include the following:

A guide device adapted to couple to a bone plate and the guide device adapted for selectively establishing a reference line having a fixed insertion point and adjustable trajectory, the guide device defining:

a first axis arranged substantially perpendicular to the bone plate;

a second axis arranged at an acute angle to the first axis;
at least one (a first) drill-guide through hole arranged parallel to the second axis whereby an alignment reference line orthogonal to the at least one drill-guide through hole intersects a plane established by the bone plate but is offset from the bone plate.

A method for aligning the syndesmosis joint including the tibia bone and fibula bone, the method comprising:
providing a bone plate and positioning the bone plate on the posterolaterial aspect of the distal fibula of the distal fibula;
the bone plate thereby defining a first plane;
establishing a first axis arranged substantially perpendicular to the first plane;
establishing a second axis arranged at an acute angle to the first axis whereby the second axis intersects the first plane but does not intersect the bone plate;
providing a first drill-guide hole arranged parallel to the second axis, the first drill-guide hole establishing an entry point, an exit point, and orientation whereby the orientation is substantially parallel to the syndesmosis joint, the entry point disposes substantially at the center of the lateral fibula and the exit point disposes substantially at the center of the medial tibia;
placing a fixation device along the second axis whereby the fixation device is located at a first distance from the syndesmosis joint and the fixation device is substantially parallel to the syndesmosis joint.

DRAWING

Figure 2:
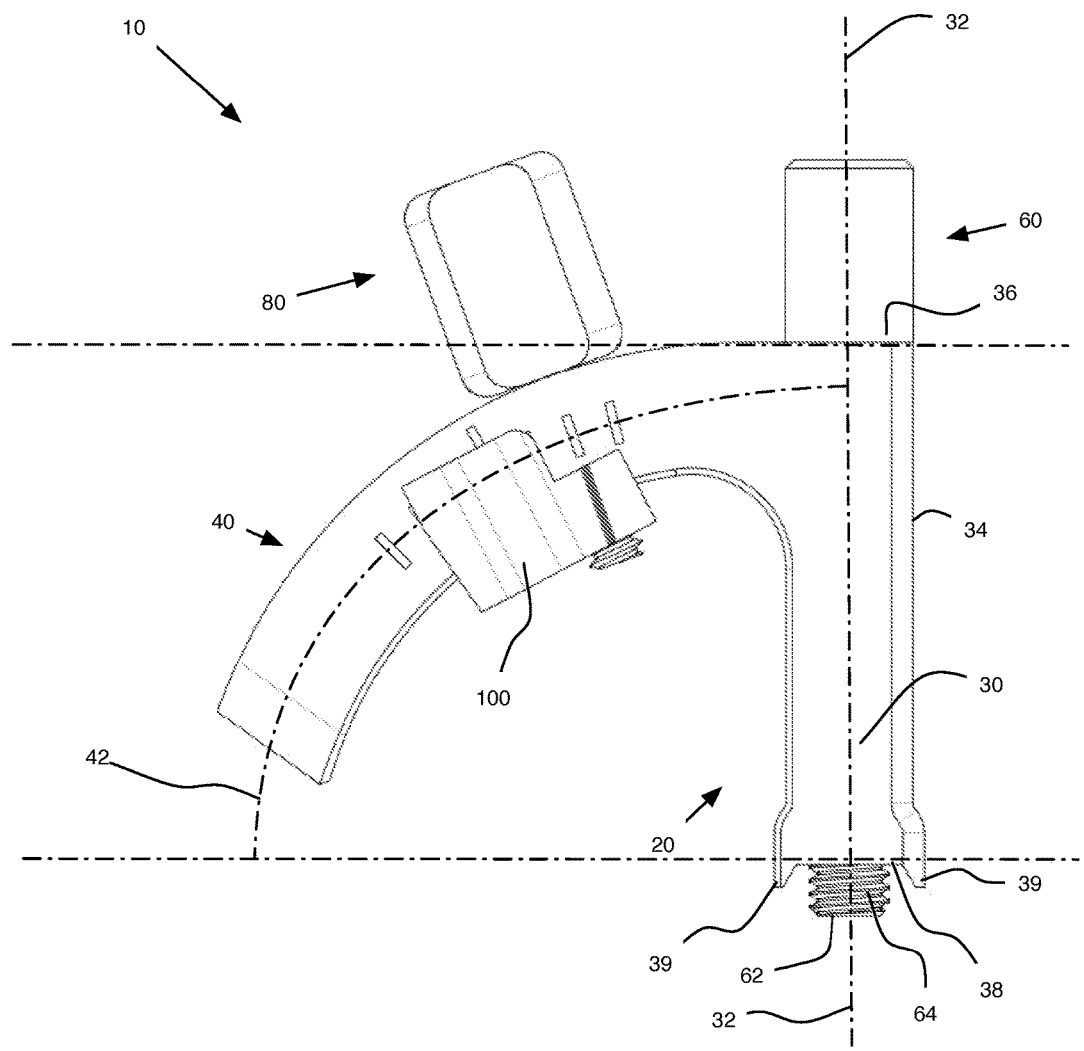
Figure 4:
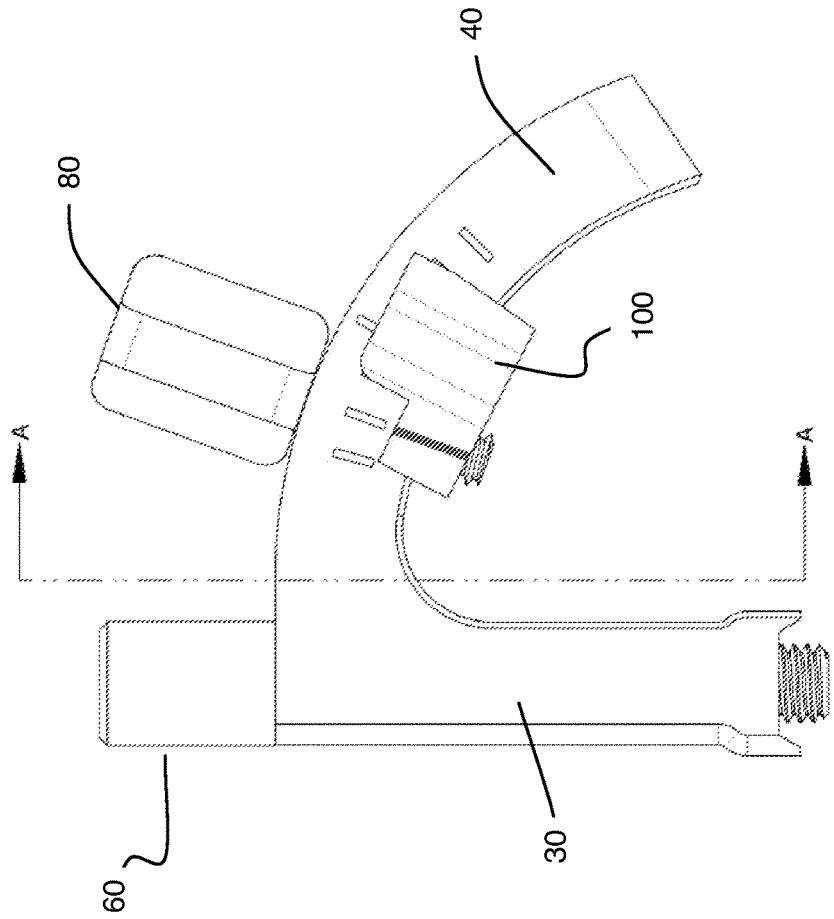
Figure 5:
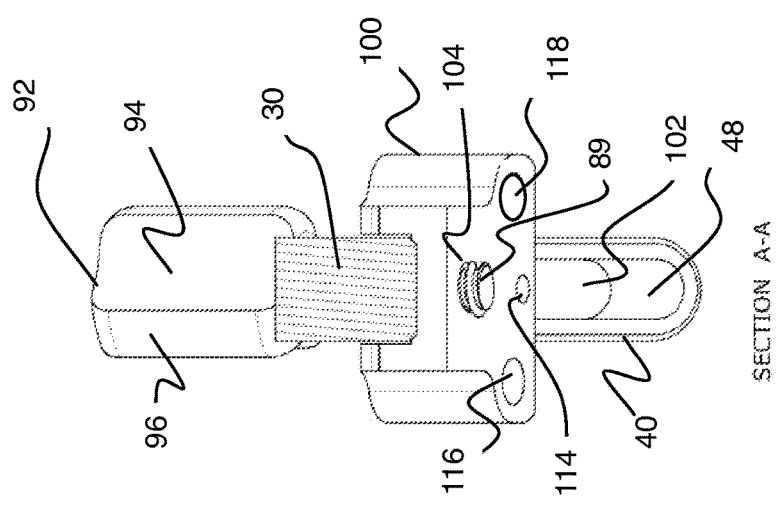
Figure 6:
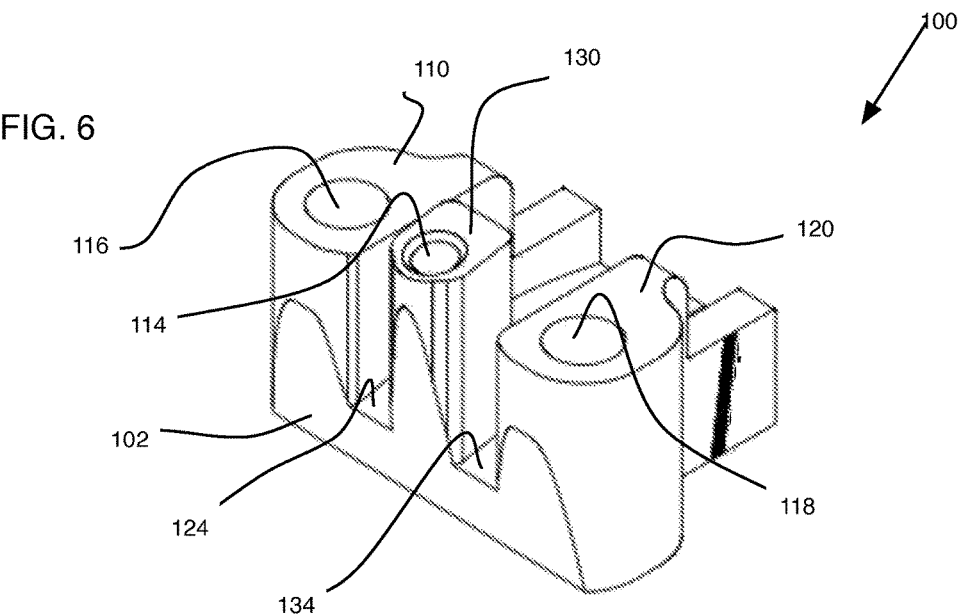
Figure 7:
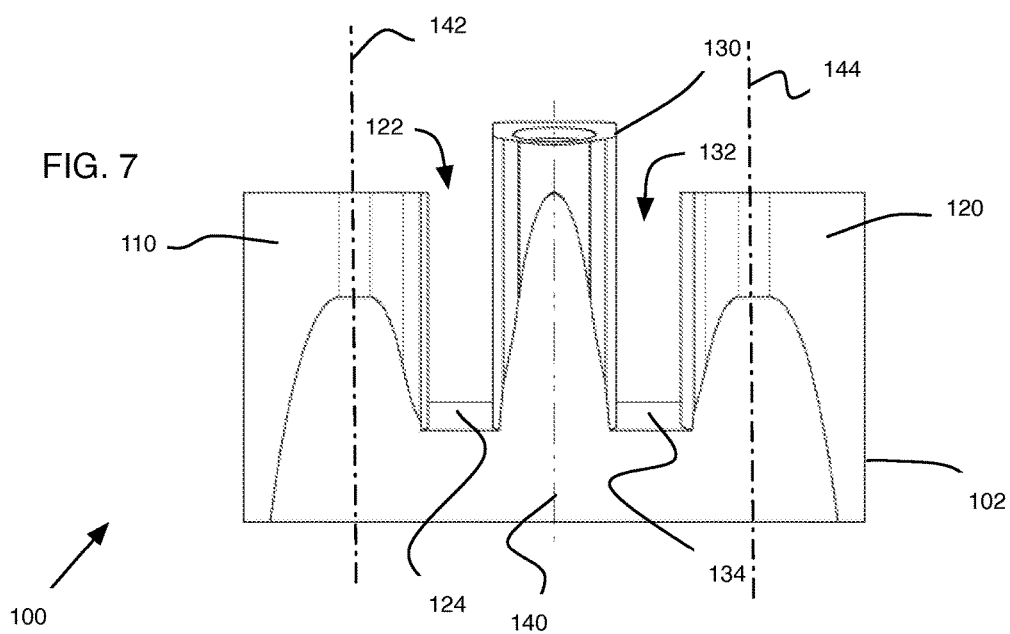
Figure 10:
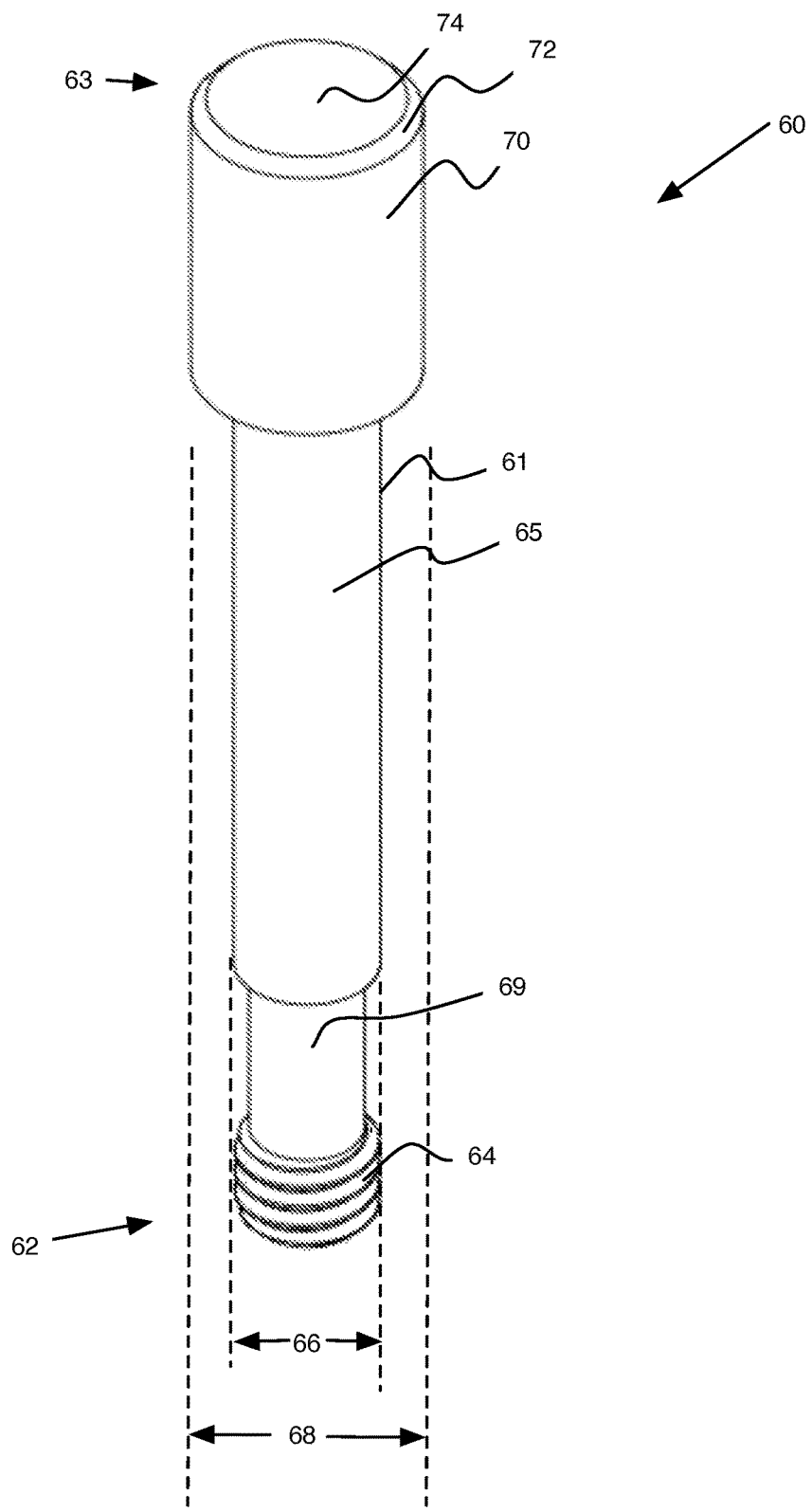
Figure 11:
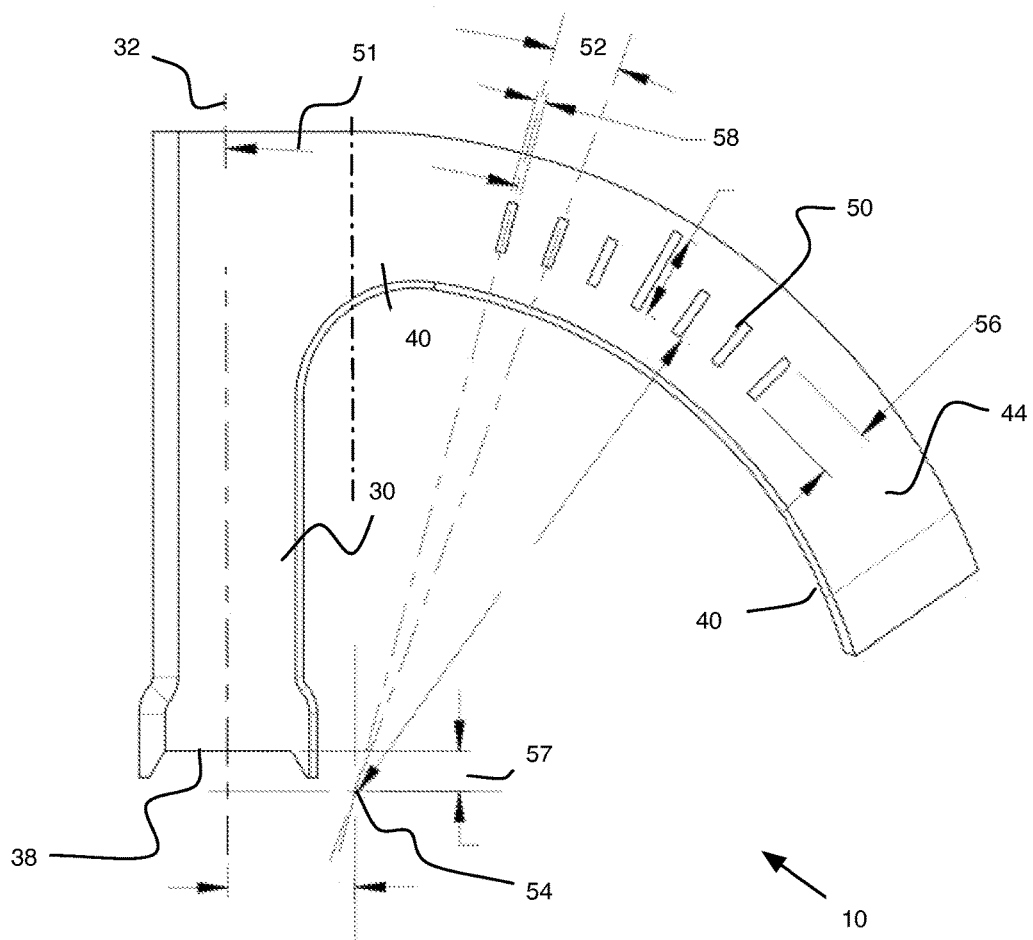
Figure 12:
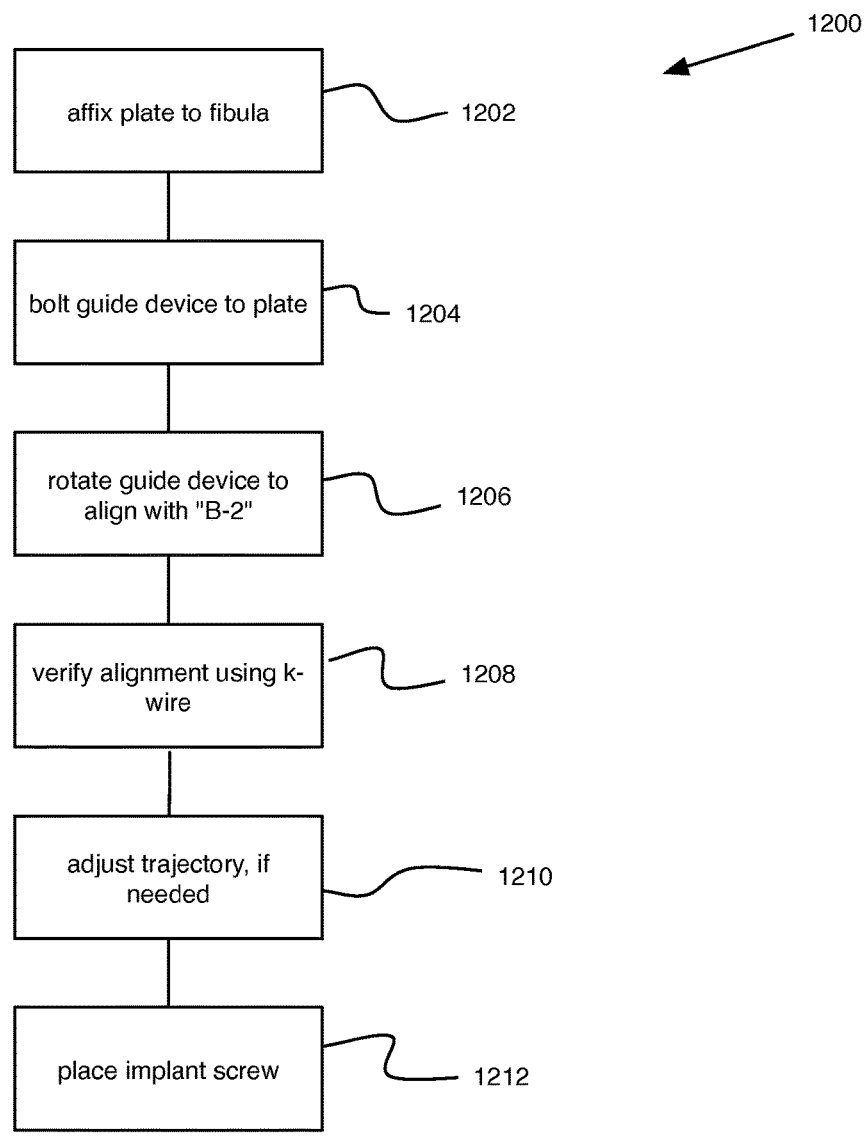
Figure 13:
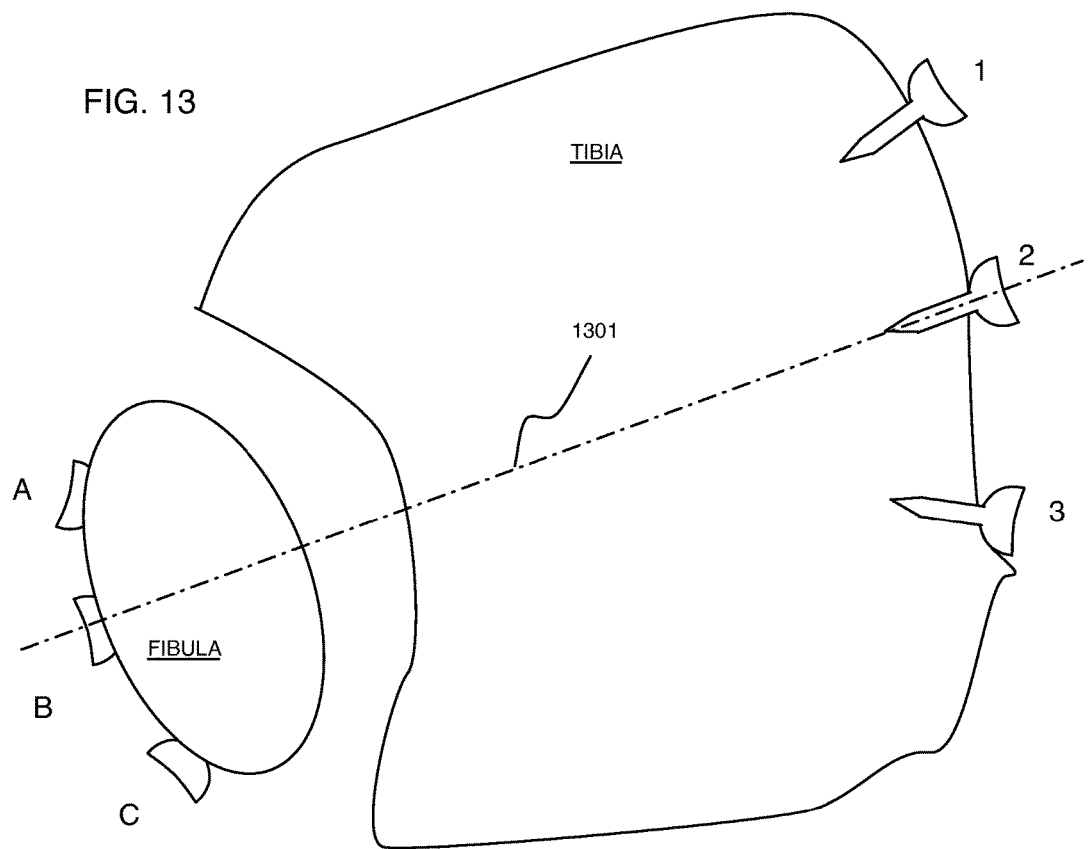
Figure 14:
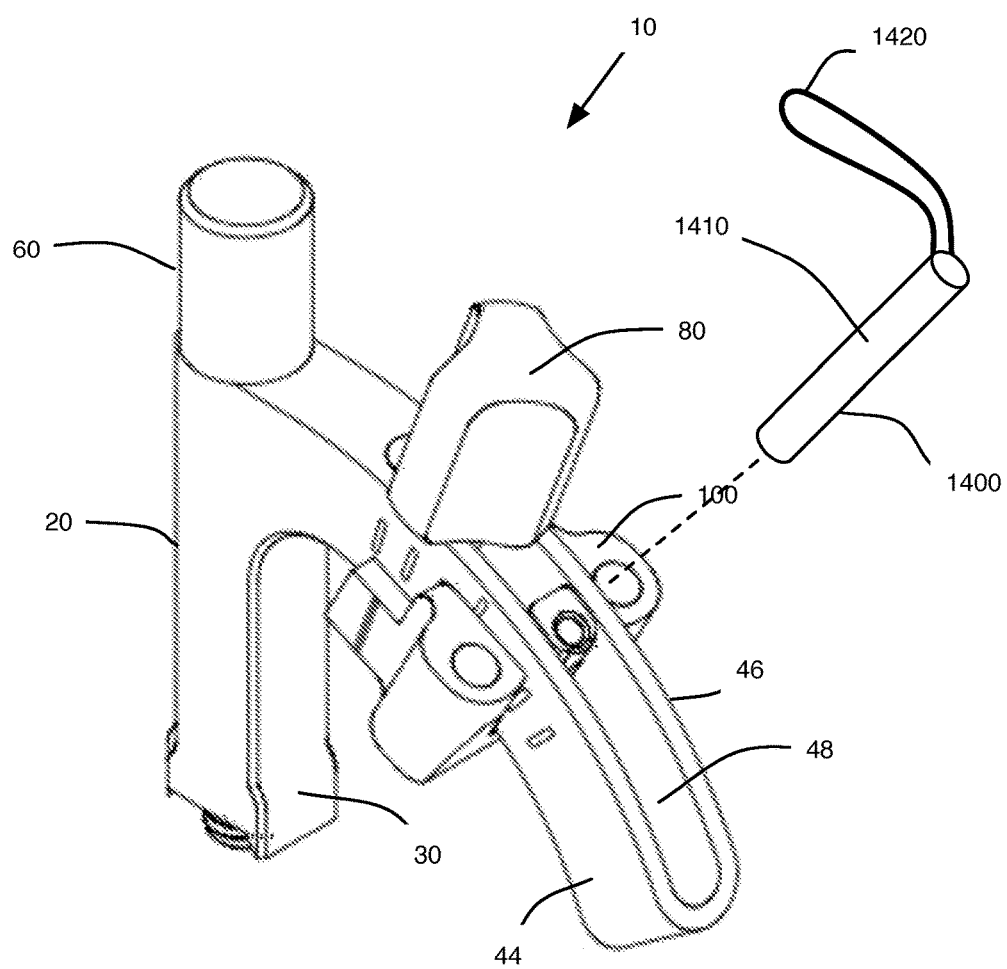
Figure 15:
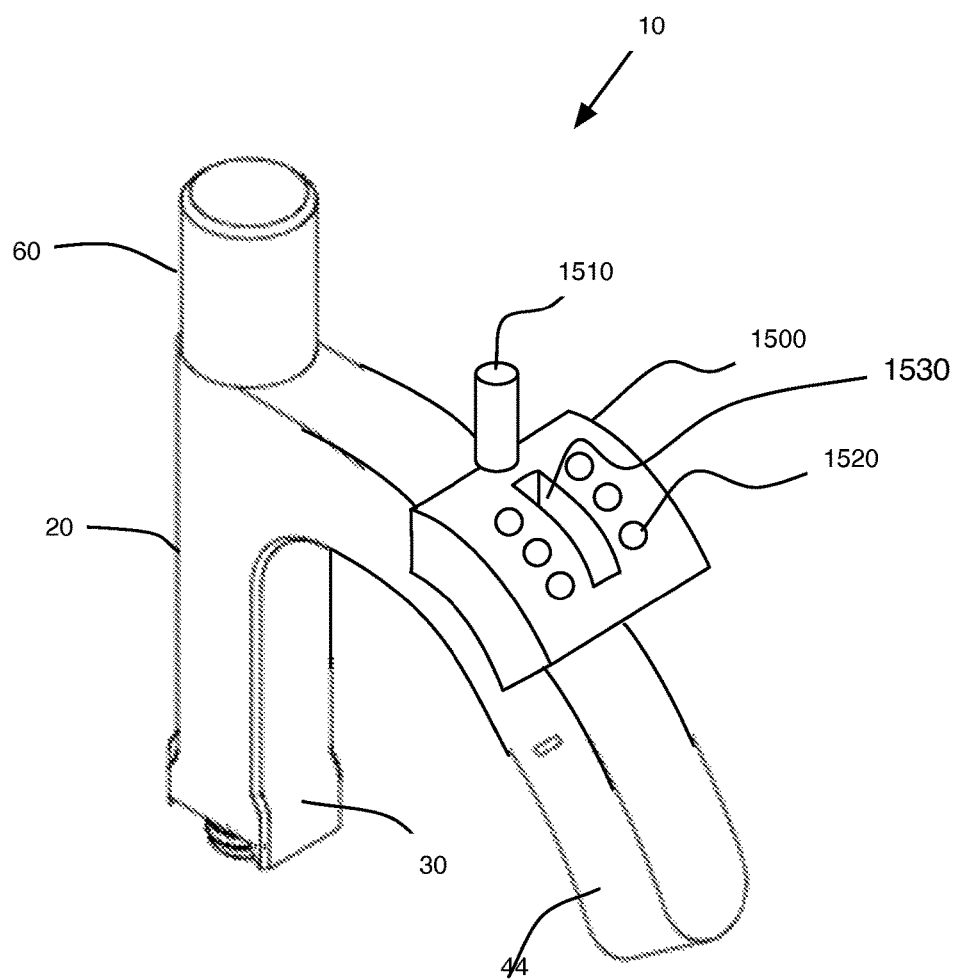

FIG. 1 is an offset frontal view of a syndesmosis guide device according to one preferred embodiment of the present invention.
FIG. 2 is right side profile view of the device of FIG. 1.
FIG. 3 is left side profile exploded view of the device of FIG. 1.
FIG. 4 is another left side profile view of the device of FIG. 1.
FIG. 5 is a frontal cross sectional view of the device along the line A-A of FIG. 4.
FIG. 6 is an offset frontal view of a slider of the device of FIG. 1.
FIG. 7 is a front view of the slider of FIG. 6.
FIG. 8 is a top view of the slider of FIG. 6.
FIG. 9 is a cross sectional view along the 9-9 of FIG. 8.
FIG. 10 is an offset frontal view of a plate bolt of the device of FIG. 1.
FIG. 11 is another left side view of the device of FIG. 1 and illustrates guide marks disposed on the guide body.
FIG. 12 is a representation of a method according to the present invention.
FIG. 13 is representation of the tibia and fibular bones and shows a preferred axis of alignment for a syndesmosis implant.
FIG. 14 is an offset frontal view of an alternative embodiment of the present invention.
FIG. 15 is an offset frontal view of yet another alternative embodiment of the present invention.
FIG. 16 is a diagram representing a first nominal plane and a transverse plane.
FIG. 17 is a schematic diagram of a method according to the present invention whereby a first nominal plane is referenced with a perpendicular transverse (second) plane having a curved arc segment, axis, and desired trajectory all in the second plane.

Figure 18:
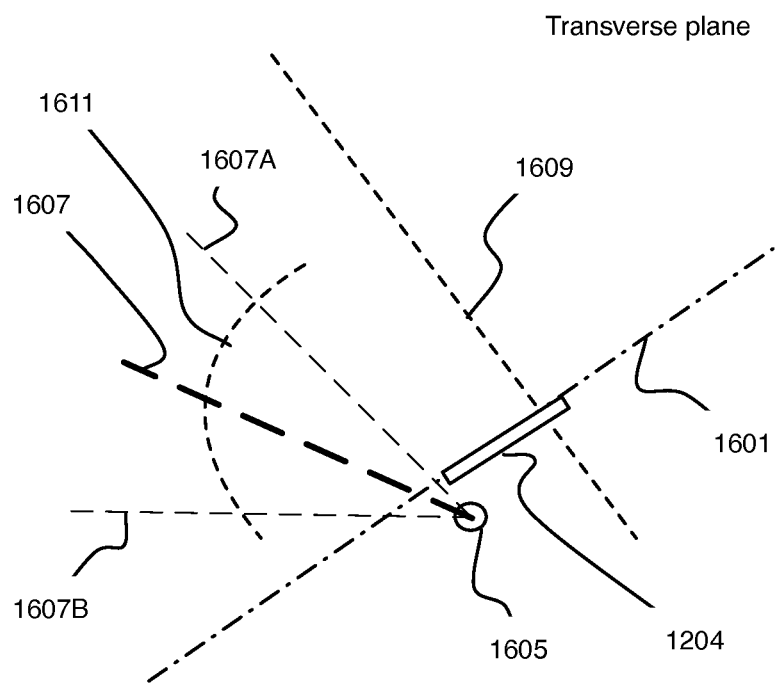
Figure 19:
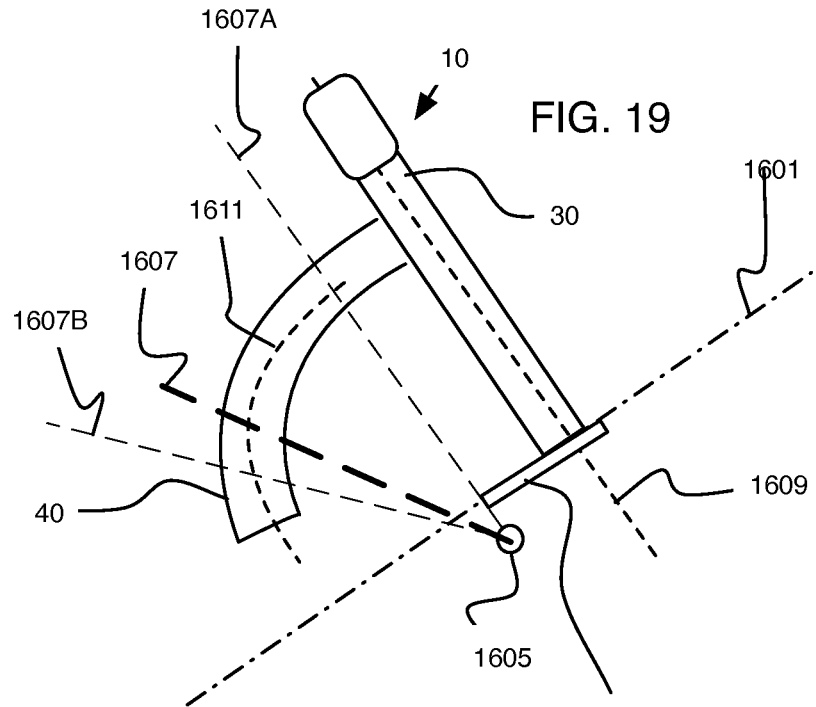

FIG. 18 is a top view of the transverse plane of FIG. 17 showing the desired trajectory relative to a bone plate arranged in the first nominal plane.
FIG. 19 is a top view of the transverse plane of FIG. 17 with a syndesmosis guide device according to one embodiment of the present invention wherein the guide device is arranged in the second plane.
FIG. 20 is a top view of the transverse plane of FIG. 17 in relation to a fibula bone and tibia bone and shows the desired trajectory in the second plane as the desired trajectory passes through the fibula and tibia.

DESCRIPTION OF THE INVENTION

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

The present invention, in various contemplated preferred embodiments, enables a surgeon to accurately and repeatably place syndesmosis implants. In the current art, difficulties properly reducing and fixating a disruption of the syndesmosis remain a common challenge. Further, even with proper reduction, inaccurate placement of the syndesmosis implant is common: Often the implant is placed too anterior or posterior of the fibula or tibia resulting in the fixation device to translate the fibula and thus resulting in malreduction of the tibio-fibular joint.

For example, common limitations in this art include the use of solid screws because cannulated screws are too weak for syndesmosis repair. Because solid screws are used, an over-the-wire technique used with cannulated screws cannot be used. Thus, multiple attempts to probe for ideal trajectory of the implant by drilling over and over, is not possible. Further, the distance required to drill to depth is relatively large. The typical syndesmosis screw is around 40 mm so a small misalignment can result is a clinically significant mal alignment. Also, there is no way to use typically available operating room fluoroscopy to ensure that the drill is targeted at the center of the medial tibia. And even after insertion of the implant it is not possible to ensure proper fixation of the syndesmosis without a cross-sectional view using CT.

To overcome these limitations, the present invention includes a novel targeting guide device that better ensures proper alignment of the implant by attaching the guide device to a pre-installed bone plate affixed to the fibula. This device, once attached to the bone plate, enables precise alignment and control of the drill trajectory, which is set to target the center of the fibula running parallel to the articular surface of the joint and allowing for adjustable targeting of the medial tibia and adjustability in the distance the implant is placed from the articular surface of the ankle joint.

In essence, the present invention contemplates a guide device that enables a surgeon to precisely place a fastening device relative to the syndesmosis joint to enable proper healing. As such, the guide device of the present invention is adapted to couple to a bone plate and the guide device is further adapted for selectively establishing a reference line having a fixed insertion point and adjustable trajectory. Thus, the guide device defines a first, nominal plane arranged substantially perpendicular to the bone plate; a transverse or second plane intersects and is perpendicular to the first plane and has a corresponding axis that lies in the second plane and is perpendicular to the first plane; an arc segment lies in the second plane intersecting with the axis, a desired trajectory lies in the second plane, intersects the first plane and is further defined at an acute angle to the first axis; and at least one (a first) drill-guide through hole arranged in line with the desired trajectory, or a pair of drill guide through holes that lie in separate (two) parallel planes parallel to the transverse plane and (both) perpendicular to the nominal first plane; this desired trajectory (or trajectories) enabled by the at least one drill-guide through hole intersects the first plane established defined by the bone plate but is offset (does not intersect) from the bone plate. This enables placement of a fixation device that is substantially parallel to the syndesmosis joint, but is offset therefrom.

The guide device of the present invention, an articulating syndesmosis guide, includes a number of features that enable accurate and repeatable placement of syndesmosis implants. The guide targets between 20-60 degrees based on a review of CT images and various development and validation labs with surgeons. The guide can be attached at multiple locations on the posterolateral fibula plate allowing for adjustment in distance from the articular surface. The slider body can be locked once the desired angle is achieved. A K-wire hole in the center allows for verification of alignment without compromising the bone for final solid screw fixation. The fixed body of the guide is a radiolucent PEEK material to help with visibility of the targeted region. The guide has multiple drill guide holes to ensure that when more than 1 screw is placed they will run in parallel. Finally, the guide targets the scalloped edge of the plate ensuring the screws nest against the plate.

In the various embodiments, the guide device 10 comprises a radiolucent PEEK material to help with visibility of the targeted region, as would be well appreciated by those skilled in the art. Other materials commonly used in this art are also contemplated.

Guide Device

In a first preferred and contemplated embodiment, the present invention includes an articulated guide device 10 particularly well adapted for use in placing a syndesmosis implant in precise alignment relative to a desired alignment axis constructed between two points on the tibia and fibula (this line is the desired trajectory). With general reference to FIGS. 1-11, this guide device 10 consists or comprises a guide body 20 comprising a post 30 extending vertically (up and down on the page having the drawings). The post 30 includes a vertical centerline (constructed as reference line 32), at least one sidewall 34, and oppositely disposed top end 36 and a bottom end 38. The bottom end further includes a scalloped feature 39 adapted to engage a corresponding and mating feature provided by a conventional bone plate such as a fibula bone plate available from Acumed LLC of Hillsboro, Oreg., USA.

Adjacent to and extending from the top end (horizontally, right to left in FIG. 2, for example), a curvilinear slider guide 40 arches downward from the top end of the post. The slider guide 40 extends along an arc 42 for greater than 20 degrees from the post 30. With specific reference to FIG. 11, this arc 42 shares a top edge of the post's top end 36 and extends from the left of the page to the right in an arcuate and downward path wherein zero-degrees of arc length begins at constructed reference line that is parallel to the vertical axis 32 of the post and extends at least to 20-degrees, more preferably past 60-degrees, and less than 90-degrees of arc length where 90-degrees would define a line perpendicular to a bottom edge of the post. Further, the curvilinear slider guide 40 includes two substantially and generally parallel sidewalls (44 46) defining a slot 48. More specifically, the curvilinear slider guide arches downward from the top end of the post (see, for example, FIGS. 4 and 5) extending along an arc for greater than 20 degrees to at least 60 degrees, and more generally, the curvilinear slider guide arches downward from the top end of the post extending along an arc for greater than 20 degrees to less than 89 degrees.

In alternative embodiments, as FIGS. 14 and 15 illustrate, the guide device can include a sleeve 1400 for inserting in at least one of the guide-through holes. A sleeve 1400 includes a generally cylindrical and hollow body 1410 with open ends and at least one sidewall. A handle 1420, such as a loop of wire, couples to the body to aid in insertion and extraction of the sleeve from the guide hole.

FIG. 15 illustrates a set of guide holes 1520 that are at discrete locations on a slider body 1500. The slider body is incorporated into the slider guide 40. Alternatively, the slider body 1500 is adjustable affixed to the slider guide by means of an adjusting pin 1510. The slider body 1500 has at least one, but preferably a plurality of holes arranged at discrete locations. In one embodiment the holes are arranged in sets of parallel holes consisting of two guide holes that align in a common plane but are offset from each other. A slot 1530 arranged between the plurality of parallel holes allows trajectory determination using a K-wire or guide wire.

The guide device 10 further includes a plate bolt 60 configured to insert through the post 30 of the guide body 20. The plate bolt comprises a distal end 62 comprising a threaded end 64.

The guide device also includes a guide bolt 80 configured to insert through the slot 48 of the guide body, and a slider 100 configured to slideably engage the curvilinear slider guide slot 48 and further configured to be adjustably fixed in a first position by the guide bolt 80.

The curvilinear slider guide 40 further includes at least one, and preferably, a plurality of guide marks 50 arranged on an exterior face of at least one of the parallel sidewalls 44, the plurality of guide marks disposed predetermined discrete arc angles 52 (See FIG. 11, for example) having a common intersection point 54 at given location relative to the posteriolateral distal fibula. This intersection point 54, in some embodiments lies on a trajectory that avoids and targets below a bone plate on the fibula, but in other contemplated embodiments the intersection point lies on a trajectory that intersects with the associated bone plate and, accordingly, the bone plate may be configured to enable this trajectory. Each guide mark 50 can be molded as in indent, or to stand proud, on the sidewall 44, or can be etched, printed, or otherwise created, as would be well understood by those having ordinary skill in this art. The guide marks 50 can have a first height 56 and first width 58 and be substantially rectilinear in shape. The first guide mark in a set of a plurality of guide mark arranges at about 20 degrees from a vertical reference line (such as the vertical line 32 of the post 30).

With particular reference to FIGS. 6-9, and with general reference to FIGS. 1-11, the slider 100 further includes a slider body 102 machined from metal or similar material. It includes a bolt-receiving hole 104 defined by a slider bolt post 106, which is configured to receive the guide bolt 80 and this hole 104 includes a mating thread portion 108. The slider body further includes a first guidepost 110 and a second guidepost 120 and a center wire-guide post 130.

The first guide post 110 disposes on a left side of the slider body, the center wire-guide post 130 arranges at a center of the slider body and the second guide post 120 disposes on a right side of the slider body wherein the first guide post and the center wire-guide post cooperate to define a first slot-wall-guiding channel 122 and wherein the center wire-guide post and the second guide post cooperate to define a second slot-wall-guiding channel 132.

The first and second slot-wall-guiding channels further comprise, respectively, an associated bottom wall 124 and 134 and further the first and second slot-wall-guiding channels, respectively, configure to slideably engage the curvilinear slider guide slot 48 and further whereby the guide bolt is operable to selectively fixably locate the slider in at least one position, the at least one position comprising a first position relative to the guide body 40.

Further, the slider body 102 includes the center wire-guide post 130, which defines a center wire guide hole 114. And, correspondingly, the first guidepost 110 defines a first-drill guide hole 116 and the second guidepost 120 defines a second-drill guide hole 118. Each guide hole (114, 116, 118) has a corresponding alignment axis 140, 142, 144) respectively. Each alignment axis is parallel to the other alignment axes, so as the slider is positioned relative to the guide body 40, each guide hole (114, 116, 118) remains in fixed position relative to the others and provides three parallel drill guide routes into the tibia and fibula, for example. And all alignment axes (140, 142, 144) are movable in unison by movement of the slider 40 being selectively positionable in the slot 48.

The slider-bolt post 106 includes a slider-bolt alignment axis 107, which lies in a common plane with the center wire-guide post's alignment axis 140, however these respective axis are in an intersect course if extended well below the bottom surface of the slider body, as FIG. 9 illustrates, for example. This slider bolt post further configures to arrange to slide under the slot 48 of the guide body.

The guide device 10 further includes a plate bolt 60. The plate bolt 60 is a cylindrical bolt having a threaded end 64 at its distal end 62 and a handle 70 at its proximal end. As such, and as FIGS. 3 and 10 illustrate, for example, the plate bolt 60 includes a bolt body 61 consisting of an elongated cylinder comprising a proximal end 63, an intermediate shank 65 adjacent to the proximal end and the shank configured to slidably insert through the post 30. Further, the shank has a first diameter 66. The proximal end further comprising a gripping element 70 having a second diameter 68 larger than the first diameter. The distal end 62 includes a reduced diameter 69 smaller than the shank diameter 66. The handle includes a rounded edge 72 leading to a flat top 74. Additional gripping elements may be scored, machined, or otherwise included in the handle to aid gripping.

The slider bolt 80 includes a slider-bolt body 82 comprising an elongated slider-bolt-cylinder with a slider-bolt proximal end 84, an intermediate section 86 adjacent to the slider-bolt proximal end and a distal end 88. The intermediate section configures to slidably insert through the slot 48 of the guide body. The slider-bolt distal end 88 is adjacent to the intermediate section, and the slider-bolt distal end includes a threaded tip 89 adapted to selectively engage the slider 100 (at slider bolt post 106) whereby the slider is selectively fixed in at least one position relative to the guide body and is adjustable through the range provided by slot 48. Preferably, the slider adjusts to discrete locations as indicated by the guide marks 50, and a detent-feature can be provided to assist the user by feeling a "click" as the slider moves in the slot. However, it is also contemplated that the slider have infinite adjustment within the confines of the slot, and the guide marks are merely reference points to assist the user, and not positive detents that require use.

Further, the slider bolt proximal end includes comprising a handle-diameter 90 larger than a slot width of the slot 48 on the guide body to restrict the slider bolt from sliding through the slot. The slider proximal end further comprises a tri-faced handle member 92 with arcuate walls 94 intersecting adjacent face edges 96.

Method

In broad terms, the method according to one preferred embodiment of the present invention enables surgeon to precisely and correctly position a fixation device to repair the syndesmosis joint. Accordingly, this method contemplates aligning the syndesmosis joint including the tibia bone and fibula bone, by means of the following steps: Providing a bone plate and positioning the bone plate in the posterolateral groove or posterolateral aspect of the distal fibula; the bone plate thereby defining a first plane; establishing a first axis arranged substantially perpendicular to the first plane; establishing a second axis arranged at an acute angle to the first axis whereby the second axis intersects the first plane but does not intersect the bone plate; providing a first drill-guide hole arranged parallel to the second axis, the first drill-guide hole establishing an entry point, an exit point, and orientation whereby the orientation is substantially parallel to the syndesmosis joint, the entry point disposes substantially at the center of the lateral fibula and the exit point disposes substantially at the center of the medial tibia;

placing a fixation device along the second axis whereby the fixation device is located at a first distance from the syndesmosis joint and the fixation device is substantially parallel to the syndesmosis joint With specific reference to FIG. 12, one preferred and contemplated method 1200 according to the present invention includes using the aforedescribed articulating guide device 10 to properly align the syndesmosis joint relative to the tibia and fibula and insert an implants. This method begins with providing and affixing either a lateral or posterolateral fibula plate to the fibula 1202. The lateral or posterolateral fibula plate includes predetermined holes and slots and further includes a canted or chamfered edge feature. One suitable bone plate is available from Acumed LLC of Hillsboro, Oreg. Those skilled in the art will appreciate the appropriate, conventional and ordinary technique, method and tools required to fix a fibula plate to the fibula.

Provide an articulating syndesmosis guide device 10, as described in the various preferred embodiments of the present invention, above. Using the plate bolt, couple the guide device the bone plate 1204. The guide device includes a scalloped edge to better align the device relative to the canted edge feature on the plate. The threaded end of the guide's plate bolt configures to engage the threaded openings provided by the plate.

With reference to FIG. 13, the ideal alignment of a syndesmosis implant arranges on an imaginary axis extending from reference "B" to reference "2" and indicated by constructed line 1301. FIG. 13 illustrates a top cross-sectional view of the syndesmosis joint including the tibia and fibula. Lateral fibula screws (A B C) are included along with medial tibia screws 1 and 2 and 3. As would be understood in the art, the corresponding reference points for implants A, B, C, 1, 2, and 3 create constructed reference lines used by surgeons to define acceptable alignment of a syndesmosis implant.

By means of the guide's post 30 and post bolt 60, the articulating syndesmosis guide by means of the slider 100 moves along the arc defined by the curvilinear slider guide

40, which enables selective alignment of the desired trajectory through the insertion point 54 so that the desired trajectory aligns with the constructed line B2 (see FIG. 13, for example). This can be done with a lateral view aligning the metal slider body with the center of the tibia. When the holes are round and centered on the tibia the user is targeted at the "2" position.

This can be verified by placing a K-wire, or similar, through the targeting guide 1208. This also allows the user to verify that the screws will be placed parallel to the articular surface. If the K-wire does not exit the tibia at the "2" position the user can estimate the required adjustment needed to center the trajectory, remove the K-wire and adjust the trajectory 1210 by moving the slider 100 relative to the slot 48. Finally, a drill is used to create a hole along the targeted "B2" trajectory and/or an implant screw is inserted following the targeted trajectory 1212.

Other contemplated and preferred embodiments include the following:

A. A guide device comprising:
 a guide body comprising a post extending vertically, the post having a vertical centerline, at least one sidewall, and oppositely disposed top end and a bottom end; adjacent to and extending from the top end, a curvilinear slider guide arches downward from the top end of the post extending along an arc for greater than 20 degrees from the post, the curvilinear slider guide comprising two substantially and generally parallel sidewalls defining a slot;
 a plate bolt configured to insert through the post of the guide body, the plate bolt comprising a distal end comprising a threaded end;
 a guide bolt configured to insert through the slot of the guide body; and
 a slider configured to slideably engage the curvilinear slider guide slot and further configured to be adjustably fixed in a first position by the guide bolt.

B. The curvilinear slider guide of paragraph A further comprising:
 a plurality of guide marks arranged on an exterior face of at least one of the parallel sidewalls, the plurality of guide marks disposed predetermined discrete arc angles having a common intersection point at given location that intersects with the vertical centerline of the post but at a location below the bottom end of the post.

C. The slider of paragraph A further comprising:
 a slider body comprising
 a slider-bolt post configured to receive the guide bolt;
 a first guide post and a second guide post and a center wire-guide post; the first guide post disposed on a left side of the slider body, the center wire-guide post disposed at a center of the slider body and the second guide post disposed on a right side of the slider body wherein the first guide post and the center wire-guide post cooperate to define a first slot-wall-guiding channel and wherein the center wire-guide post and the second guide post cooperate to define a second slot-wall-guiding channel;
 the first and second slot-wall-guiding channels further comprising, respectively, an associated bottom wall and further the first and second slot-wall-guiding channels, respectively, configure to slideably engage the curvilinear slider guide slot and further whereby the guide bolt is operable to selectively fixably locate the slider in at least one position, the at least one position comprising a first position relative to the guide body; and
 wherein the wire-guide post defines a wire-through hole; and wherein the slider bolt post disposes on a common plane with the center wire-guide post, the slider-bolt post further configures to arrange to slide under the slot of the guide body.

D. The slider of paragraph C wherein:
 the first guide post further defines a first-drill-guide through hole, and the second guide post further defines a second-drill-guide through hole; and
 the first-drill-guide through hole, the second-drill-guide through hole, and the post wire-through hole all having a corresponding alignment axis wherein each alignment axis is parallel to the other alignment axes and all alignment axes are movable in unison by movement of the slider being selectively positionable in the slot.

E. The plate bolt of paragraph A further comprising:
 a bolt body comprising an elongated cylinder comprising a proximal end;
 an intermediate shank adjacent to the proximal end and the shank configured to slidably insert through the post, the shank having a first diameter;
 the proximal end further comprising a gripping element having a second diameter larger than the first diameter; and
 the distal end comprising the threaded end.

F. The slider bolt of paragraph A further comprising:
 a slider-bolt body comprising a elongated slider-bolt-cylinder comprising a slider-bolt proximal end, an intermediate section adjacent to the slider-bolt proximal end and the intermediate section configured to slidably insert through the slot of the guide body, and a slider-bolt distal end adjacent to the intermediate section, the slider-bolt distal end comprising a threaded tip adapted to selectively engage the slider whereby the slider is selectively fixed in at least one position relative to the guide body;
 and
 a slider proximal end further comprising a handle-diameter larger than a slot width of the slot on the guide body to restrict the slider bolt from sliding through the slot.

G. The slider bolt of paragraph F further comprising:
 the slider proximal end further comprising a tri-faced handle member with arcuate walls intersecting adjacent face edges.

H. The guide body of paragraph A further comprises:
 wherein curvilinear slider guide arches downward from the top end of the post extending along an arc for greater than 20 degrees to at least 60 degrees.

I. The guide body of paragraph A further comprises:
 wherein curvilinear slider guide arches downward from the top end of the post extending along an arc for greater than 20 degrees to less than 89 degrees.

J. An articulating syndesmosis guide device configured to selectively couple to a bone plate, the device comprising:
 a guide body comprising
  a post extending vertically, the post having a vertical centerline, at least one sidewall, and oppositely disposed top end and a bottom end;
  a curvilinear slider guide arranges adjacent to and extending from the top end, the curvilinear slider guide further arches downward from the top end of the post extending along an arc for greater than 20 degrees from the post, the curvilinear slider guide comprising two substantially and generally parallel sidewalls defining a slot, and the bottom end further comprising a scalloped feature configured to mate to a corresponding feature provided by the bone plate;
  a plate bolt configured to insert through the post of the guide body, the plate bolt comprising a distal end comprising a threaded end, the threaded end selectively engaging the plate;

a guide bolt configured to insert through the slot of the guide body; and a slider configured to slideably engage the curvilinear slider guide slot and further configured to be adjustably fixed in a first position by the guide bolt; and a slider body comprising a slider-bolt post configured to receive the guide bolt;

a first guide post and a second guide post and a center wire-guide post; the first guide post disposed on a left side of the slider body, the center wire-guide post disposed at a center of the slider body and the second guide post disposed on a right side of the slider body wherein the first guide post and the center wire-guide post cooperate to define a first slot-wall-guiding channel and wherein the center wire-guide post and the second guide post cooperate to define a second slot-wall-guiding channel;

the first and second slot-wall-guiding channels further comprising, respectively, an associated bottom wall and further the first and second slot-wall-guiding channels, respectively, configure to slideably engage the curvilinear slider guide slot and further whereby the guide bolt is operable to selectively fixably locate the slider in at least one position, the at least one position comprising a first position relative to the guide body; and wherein the wire-guide post defines a wire-through hole; and wherein the slider bolt post disposes on a common plane with the center wire guide post, the slider-bolt post further configures to arrange to slide under the slot of the guide body.

K. The guide body of paragraph J further comprises:
wherein curvilinear slider guide arches downward from the top end of the post extending along an arc for greater than 20 degrees to at least 60 degrees.

L. The guide body of paragraph J further comprises:
wherein curvilinear slider guide arches downward from the top end of the post extending along an arc for greater than 20 degrees to less than 89 degrees.

M. The slider of paragraph J wherein:
the first guide post further defines a first-drill-guide through hole, and the second guide post further defines a second-drill-guide through hole; and
the first-drill-guide through hole, the second-drill-guide through hole, and the post wire-through hole all having a corresponding alignment axis wherein each alignment axis is parallel to the other alignment axes and all alignment axes are movable in unison by movement of the slider being selectively positionable in the slot.

N. A method for aligning the syndesmosis joint including the tibia bone and fibula bone, the method comprising:
providing a bone plate comprising one or more threaded holes, one or more slots, and at least one scalloped edge feature;
providing an articulated syndesmosis guide, the guide comprising
a guide body comprising a post extending vertically, the post having a vertical centerline, at least one sidewall, and oppositely disposed top end and a bottom end; a curvilinear slider guide arranges adjacent to and extending from the top end, the curvilinear slider guide further arches downward from the top end of the post extending along an arc for greater than 20 degrees from the post, the curvilinear slider guide comprising two substantially and generally parallel sidewalls defining a slot, and the bottom end further comprising a scalloped feature configured to mate to a corresponding feature provided by the bone plate; a plate bolt configured to insert through the post of the guide body, the plate bolt comprising a distal end comprising a threaded end, the threaded end selectively engaging the plate; a guide bolt configured to insert through the slot of the guide body; and a slider configured to slideably engage the curvilinear slider guide slot and further configured to be adjustably fixed in a first position by the guide bolt; and a slider body comprising a slider-bolt post configured to receive the guide bolt;

a first guide post and a second guide post and a center wire-guide post; the first guide post disposed on a left side of the slider body, the center wire-guide post disposed at a center of the slider body and the second guide post disposed on a right side of the slider body wherein the first guide post and the center wire-guide post cooperate to define a first slot-wall-guiding channel and wherein the center wire-guide post and the second guide post cooperate to define a second slot-wall-guiding channel;

the first and second slot-wall-guiding channels further comprising, respectively, an associated bottom wall and further the first and second slot-wall-guiding channels, respectively, configure to slideably engage the curvilinear slider guide slot and further whereby the guide bolt is operable to selectively fixably locate the slider in at least one position, the at least one position comprising a first position relative to the guide body; and wherein the wire-guide post defines a wire-through hole; and wherein the slider bolt post disposes on a common plane with the center wire-guide post, the slider-bolt post further configures to arrange to slide under the slot of the guide body;

coupling the bone plate to the fibula;

using the plate bolt, coupling the guide device to the bone plate;

rotating the guide device about a first position to target a second position of the center of the medial tibia;

adjusting a trajectory of an implant by moving the slider relative to the slot.

O. The method of paragraph N further comprising:
providing a K-wire;
using the K-wire, determining an alignment axis of the implant.

P. The method of paragraph N further comprising:
providing a drill;
using the drill, placing an implant screw using the guide device to align the implant screw.

Q. The method of paragraph N wherein:
the slider further comprising the first guide post further defines a first-drill-guide through hole, and the second guide post further defines a second-drill-guide through hole; and
the first-drill-guide through hole, the second-drill-guide through hole, and the post wire-through hole all having a corresponding alignment axis wherein each alignment axis is parallel to the other alignment axes and all alignment axes are movable in unison by movement of the slider being selectively positionable in the slot.

R. A guide device adapted to couple to a bone plate and the guide device adapted for selectively establishing a reference line having a fixed insertion point and adjustable trajectory, the guide device defining:
a first axis arranged substantially perpendicular to the bone plate;
a second axis arranged at an acute angle to the first axis;
at least one (a first) drill-guide through hole arranged parallel to the second axis whereby an alignment reference line orthogonal to the at least one drill-guide through hole intersects a plane established by the bone plate but is offset from the bone plate.

S. A method for aligning the syndesmosis joint including the tibia bone and fibula bone, the method comprising:

providing a bone plate and positioning the bone plate in the posterolateral groove of the distal fibula;

the bone plate thereby defining a first plane;

establishing a first axis arranged substantially perpendicular to the first plane, the first axis lies in a second plane, the second plane perpendicular to the first plane;

establishing a second axis in the second plane, the second axis arranged at an acute angle to the first axis whereby the second axis intersects the first plane but does not intersect the bone plate;

providing a first drill-guide hole arranged parallel to the second axis, the first drill-guide hole establishing an entry point, an exit point, and orientation whereby the orientation is substantially parallel to the syndesmosis joint, the entry point disposes substantially at the center of the lateral fibula and the exit point disposes substantially at the center of the medial tibia;

placing a fixation device along the second axis whereby the fixation device is located at a first distance from the syndesmosis joint and the fixation device is substantially parallel to the syndesmosis joint.

FIGS. 16-20 illustrate another preferred method according to the present invention. Accordingly, this method aligns and fixes the syndesmosis joint and includes a fixation device passing through the tibia bone T and the fibula bone F along a desired axis 1607 (or axis 1301 of FIG. 13, for example) determined by the surgeon. This method 1600 includes establishing a first, nominal plane 1601 arranged parallel to the posterolateral groove or aspect of the distal fibula. Establishing a second, transverse plane 1603 arranged perpendicular to the first, nominal plane. Providing a fixed entry point 1605 in the fibula wherein the fixed entry point lies in the second plane. Establishing a desired trajectory 1607 in the second plane wherein the trajectory includes the fixed entry point, and inserting a fixation device along the desired trajectory.

To achieve this method, a guide device, such as a syndesmosis targeting guide 10 as previously described (above) is provided. Such a device would include a guide body comprising a post 30 having a post axis 1609 extending perpendicular to a first nominal plane 1601 and the post axis 1609 arranges in a second transverse plane 1603, which is perpendicular to the first nominal plane 1601. The guide body further comprises a curvilinear slider guide 40 extending along an arc 1611 in the second plane. The arc intersects the post axis. And, a slider 100 (see FIGS. 1-11) configured to slideably engage along the arc 1611 to at least a first position.

This method 1600 and device 10 work together to enable a desired trajectory 1607 that extends through the posterolateral fibula at an insertion point 1605 and continues through the fibula F and tibia T. The guide device 10 enables the surgeon to determine at least a first desired trajectory 1607 in the second plane (transverse) plane 1603. The guide device 10 includes a curved slider guide 40 that enables positioning of the desired trajectory along the arc 1611 from a first position 1607A to a second position 1607B, or from substantially about parallel to the axis 1609 to about 75 degrees (1607B), preferable around 45-degrees offset from the axis 1609, wherein each of these possible trajectories include the common insertion point 1605 and all lie in the common second plane. The slider guide 100, in certain preferred embodiments discuss above, includes two parallel guide holes that establish a respective third and fourth plane that are parallel to the second plane.

Although the invention has been particularly shown and described with reference to certain embodiments, it will be understood by those skilled in the art that various changes in form and detail may be made without departing from the spirit and scope of the invention.

We claim:

1. A method of fixing a syndesmosis joint between a fibula and a tibia, the method comprising:

attaching a bone plate to the fibula;

coupling a targeting device to the fibula via the bone plate, the targeting device defining a guide axis lying in a plane transverse to a longitudinal axis of the fibula, a portion of the guide axis extending through the fibula between the targeting device and the tibia, an orientation of the guide axis with respect to the fibula being adjustable in the plane while the targeting device remains coupled to the fibula via the bone plate; and inserting a fixation device into the fibula and the tibia on a trajectory corresponding to the guide axis.

2. The method of claim 1, wherein the step of attaching a bone plate includes a step of attaching the bone plate to a distal, posterolateral aspect of the fibula.

3. The method of claim 1, wherein the step of coupling a targeting device includes a step of attaching the targeting device to the bone plate with a bolt having a threaded distal end to engage the bone plate.

4. The method of claim 1, wherein the targeting device includes a body and a slider, and wherein the body defines an arc, the method further comprising a step of moving the slider along the arc to adjust the orientation of the guide axis in the plane.

5. The method of claim 4, further comprising a step of locking the slider to the body to fix the orientation of the guide axis in the plane.

6. The method of claim 1, wherein the orientation of the guide axis is configured to be adjustable in the plane about a fixed point.

7. The method of claim 6, wherein the step of inserting includes a step of inserting the fixation device into the fibula at the fixed point.

8. The method of claim 1, wherein the bone plate has a perimeter, and wherein the guide axis extends past the bone plate outside the perimeter.

9. The method of claim 8, wherein the step of inserting a fixation device includes a step of nesting the fixation device against a scalloped edge of the bone plate.

10. The method of claim 1, further comprising a step of drilling holes in the fibula and tibia along the guide axis, wherein the step of inserting includes a step of inserting the fixation device into the holes.

11. The method of claim 1, wherein the targeting device is configured to guide drilling into the fibula along a pair of separate guide axes that are parallel to one another and the plane, and that are located at different longitudinal positions relative to one another along the fibula.

12. The method of claim 1, wherein the step of inserting a fixation device includes a step of inserting a screw into the fibula and the tibia on the trajectory.

13. The method of claim 1, further comprising a step of placing a guide wire into the fibula and the tibia along an axis parallel to the guide axis.

14. The method of claim 13, wherein the axis parallel to the guide axis is separate from the trajectory of the fixation device.

15. The method of claim 13, wherein the step of placing a guide wire is performed before the step of inserting a fixation device, to verify a trajectory of the guide axis through the fibula and tibia.

16. The method of claim 15, wherein a leading end of the guide wire exits the tibia at a medial side thereof.

17. The method of claim 1, wherein the targeting device is configured to be attached to the bone plate at alternative locations on the bone plate.

18. A method of fixing a syndesmosis joint between a fibula and a tibia, the method comprising:
- attaching a bone plate to the fibula;
- coupling a targeting device to the fibula via the bone plate, such that the targeting device defines a guide axis lying in a plane transverse to a longitudinal axis of the fibula;
- sliding a slider of the targeting device translationally along an arc defined by a curved slider guide, the arc lying in the plane, to adjust an orientation of the guide axis in the plane;
- drilling the fibula and the tibia along the guide axis; and
- inserting a fixation device into the fibula and the tibia on a trajectory corresponding to the guide axis.

19. The method of claim 18, wherein the step of moving a slider includes a step of moving the slider to a discrete location determined by a detent of the targeting device.

20. A method of fixing a syndesmosis joint between a fibula and a tibia, the method comprising:
- attaching a bone plate to the fibula;
- coupling a targeting device to the fibula via the bone plate, such that the targeting device defines a guide axis lying in a plane transverse to a longitudinal axis of the fibula, an orientation of the guide axis being adjustable in the plane while the targeting device remains coupled to the fibula;
- placing a guide wire into the fibula and the tibia from the targeting device along an axis parallel to the guide axis and the plane, wherein the guide wire enters the fibula before the tibia;
- drilling the fibula and the tibia along the guide axis; and
- inserting a fixation device into the fibula and the tibia on a trajectory corresponding to the guide axis.

* * * * *